United States Patent [19]

Eisenkraft

[11] 4,447,141
[45] May 8, 1984

[54] VISION TESTING SYSTEM

[76] Inventor: Arthur Eisenkraft, 7 Iroquois Rd., Ossining, N.Y. 10562

[21] Appl. No.: 375,805

[22] Filed: May 7, 1982

[51] Int. Cl.$^3$ ............................................. A61B 3/02
[52] U.S. Cl. .................................. 351/237; 351/243; 351/211
[58] Field of Search ................ 351/237, 243, 239, 211

[56] References Cited
U.S. PATENT DOCUMENTS
4,293,200  10/1981  Dobson et al. ...................... 351/243

Primary Examiner—John K. Corbin
Assistant Examiner—Rodney B. Bovernick
Attorney, Agent, or Firm—S. C. Yuter

[57] ABSTRACT

A vision testing system is disclosed in which a collimated beam of coherent light waves is passed through a transparency of an object such as a grating, a Snellen letter or a portrait to produce the diffraction pattern of the object. Then the light waves forming the diffraction pattern pass through a lens to produce the Fourier transform (the diffraction pattern) at the focal plane of the lens. A variable spatial frequency filter is positioned at the focal plane. Then the spatially filtered light waves are passed through a second lens to produce the inverse of the Fourier transform at the image plane of the second lens. That image is the spatially filtered object. By varying the degree and type of spatial filtering the resultant image can be used to test for contrast sensitivity or character (object) recognition.

25 Claims, 12 Drawing Figures

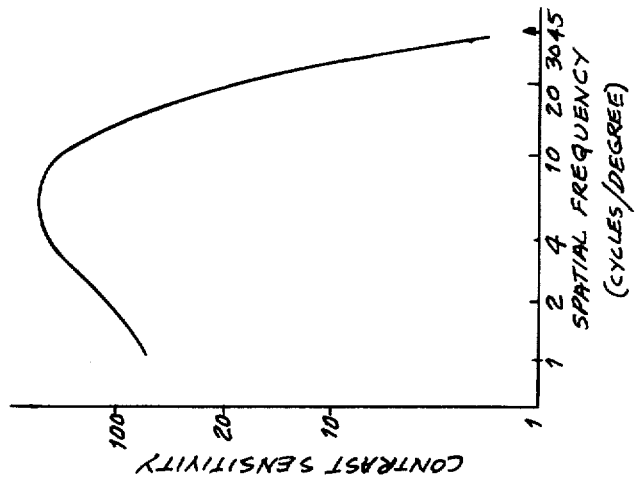
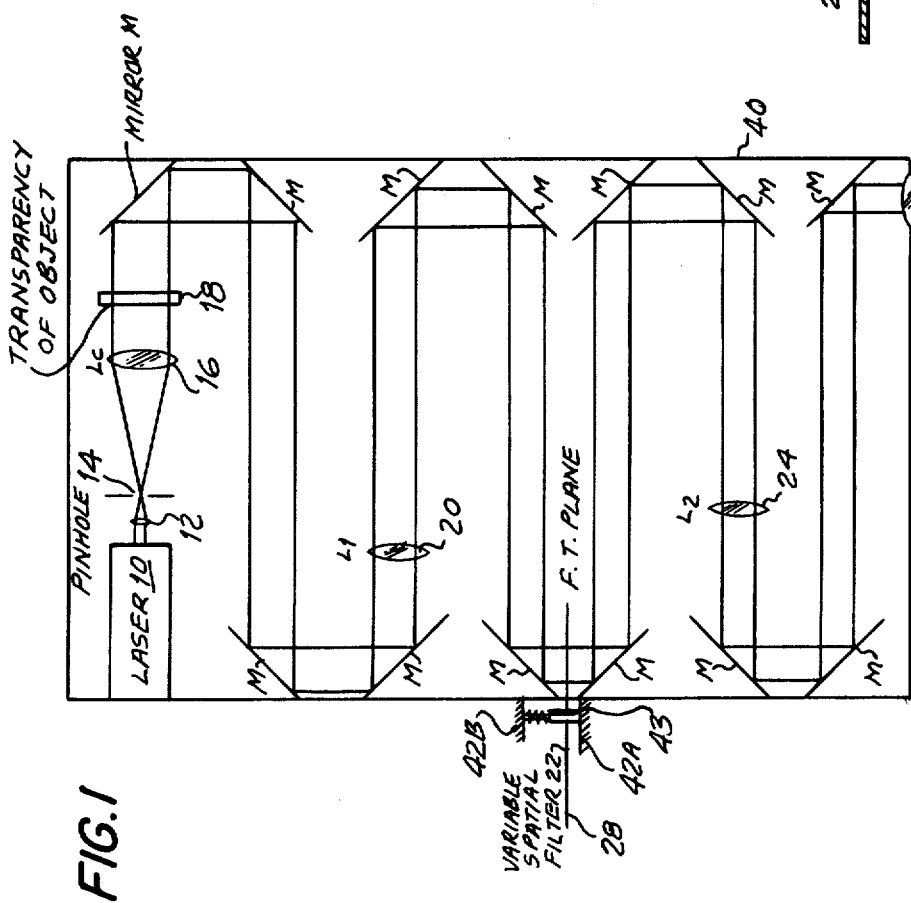
FIG.1
FIG.1A
FIG.1B
FIG.2

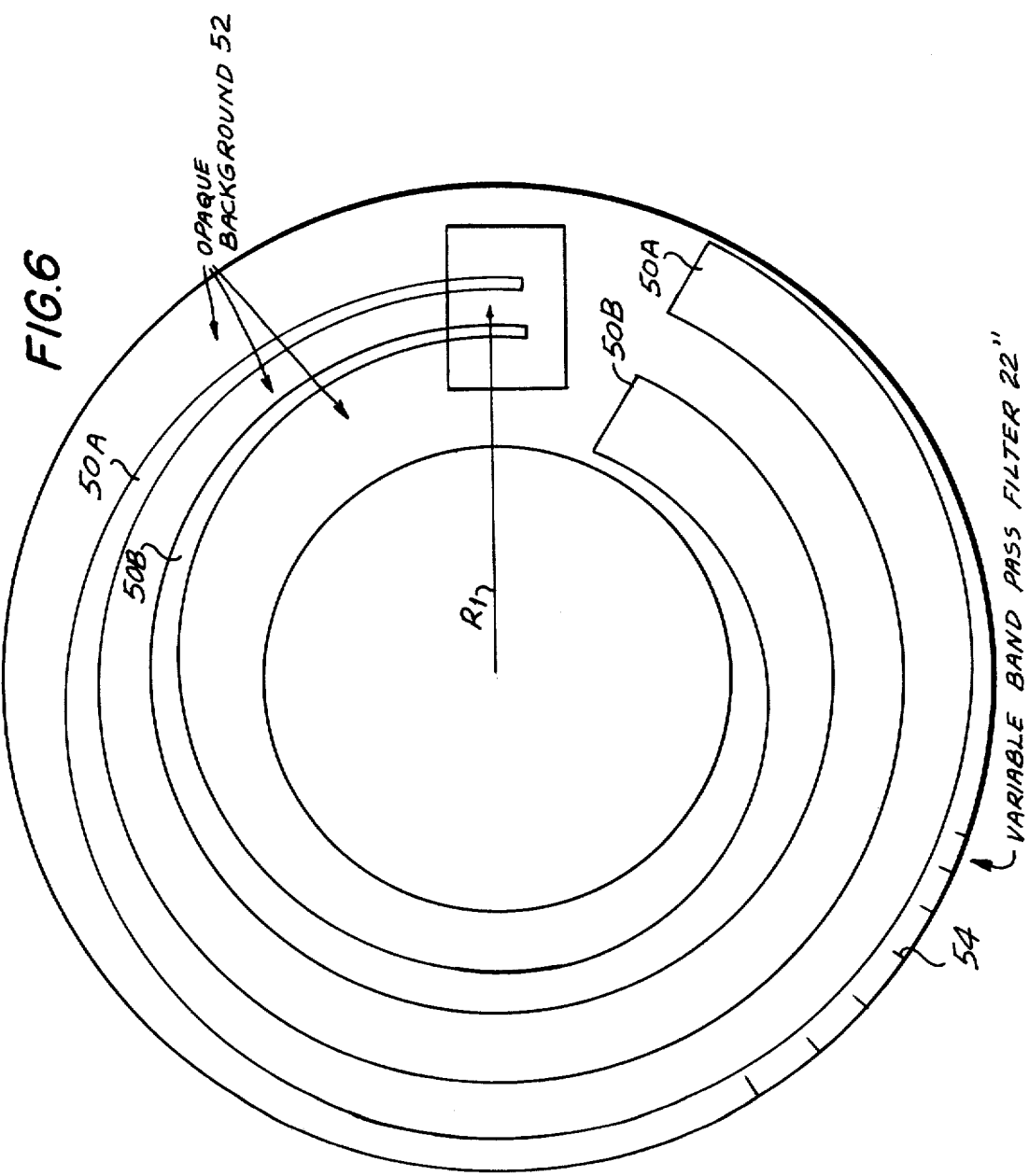

VISION TESTING SYSTEM

FIELD OF THE INVENTION

This invention relates to vision testing systems and, more particularly, to systems for testing vision contrast sensitivity and object recognition.

BACKGROUND OF THE INVENTION

Recent experimental evidence has shown that the Snellen acuity test which is popularly used for testing vision is inadequate for identifying certain abnormalities in an individual's vision. Although the Snellen test can reveal what size letter a person can recognize, it has no means for measuring the level of contrast necessary for letter recognition.

Contrast can be qualitatively equated to the degree of sharpness in a photocopy of a document. In a high quality photocopy (high contrast) the black letters stand out from the white background. In a poor quality photocopy (low contrast) the dark letters are barely discernible over the light gray background.

Reduced contrast sensitivity, due to abnormal spatial frequency channels, may explain vision dimness and other vision abnormalities. There is firm evidence that certain patients suffering from multiple sclerosis complain about the quality of vision in one eye compared to another when both eyes test as having normal Snellen acuity. However, when contrast sensitivity is measured, the reduced sensitivity explains why an otherwise normal eye has impaired vision. This suggests that contrast sensitivity measurements may be an early diagnostic aid in some patients suspected to have multiple sclerosis.

Abnormal spatial frequency channels and consequent reduced contrast sensitivity may explain some defects in perception including form perception.

In a study of 36 patients with cerebral lesions who complained of blurred vision, yet had 20/40 acuity or better, it was shown that the blurred vision could be explained using contrast sensitivity testing. These deficiencies could be grouped into three broad categories of loss: high frequency loss, loss at all frequencies and loss at a particular frequency.

Glaucoma patients exhibit a different contrast sensitivity defect due to glaucomatous visual damage which effects spatial frequency filtering. Thus contrast sensitivity testing could be of clinical significance concerning early therapy for glaucoma-prone eyes.

Corneal edema is a problem associated with wearing contact lenses. Contrast sensitivity measurements could provide important clinical help in evaluating the effectiveness and safety of soft contact lenses.

Some cataract patients with normal or near-normal acuity reveal a considerable low frequency deficit in contrast sensitivity while sensitivity to high spatial frequencies remains intact. Another group of cataract patients can be identified by a contrast level loss. So contrast sensitivity testing may be useful in the presurgical evaluation of these patients.

Patients suffering from retinitis pigmentosa may have a spatial frequency deficiencies much worse than Snellen acuity reveals. Such abnormalities have also been reported in several forms of macular dystrophies, also not revealed by Snellen testing.

It is also claimed that contrast sensitivity measurements have: detected early changes in the crystalline lens; predicted the mobility of low vision patients; quantified the vision of amblyopes; assessed performance changes with visual training; reflected subtle residue of acute optic neuritis; and defined visual losses from exposure to toxic substances.

DESCRIPTION OF THE PRIOR ART KNOWN TO INVENTOR

Heretofore contrast sensitivity has been measured with a digital computer and a cathode ray tube to generate different diffraction gratings of different contrasts. The subject chooses signal limits for his or her vision which are then recorded. The patterns of alternating light and dark bars computer generated on the cathode ray tube are smoothly varied from light to dark and back again. The contrast of the bars is altered without changing the average brightness of the overall pattern. As contrast changes, bright bars decrease in light level as much as the dark bars increase.

Digital computer have also been used for looking at portraits after specific spatial frequency filtering. The portrait is fed digitally into the computer and then a fast Fourier transform (explained in the detailed description of the invention which follows) is performed. Filtering is done by the computer and a resultant portrait is created. The patient's ability to recognize the portrait is a measure of the patient's contrast sensitivity.

Thus, Arthur Ginsburg of the U.S. Air Force has been vision testing by exploring recognition of complex forms, be it Snellen letters or portraits, when only limited information in spatial frequencies is given. In generating the limited bands of spatial frequency, Ginsburg has used a computer algorithm which can take the fast Fourier transform of a function (Snellen letter or portrait), eliminate all but a specific band of spatial frequencies, and produce a new function which can then be observed and used as a vision test for recognition.

The costs of these computer-based contrast sensitivity testing and character recognition systems have put them out of economic reach of most ophthalmologists, neurologists and Motor Vehicle Bureaus, which test for adequate driving vision.

SUMMARY OF THE INVENTION

The principal object of the invention is to provide a contrast sensitivity testing system well within the economic reach of ophthalmologists, optometrists, neurologists and Motor Vehicle Bureaus which test for adequate driving vision.

Another object of the invention is to provide a portable contrast sensitivity testing system.

Still another object of the invention is to provide a spatial frequency testing system in which the subject tested can manually vary the amount of spatial filtering for both optimum and minimum object recognition.

A further object of the invention is to provide a spatial frequency testing system which is versatile in being able to modify Snellen letters and other test objects conveniently and inexpensively.

Briefly, these and other objects of the invention are achieved by a vision testing system in which a collimated beam of coherent light waves is passed through a transparency of an object such as a grating, a Snellen letter or portrait to produce its diffraction pattern. Then the light waves forming the diffraction pattern pass through a lens to produce the Fourier transform (the diffracton pattern) at the focal plane of the lens. A variable spatial frequency filter is positioned at the focal plane. The spatially filtered lightwaves of the Fourier transform (the diffraction pattern) of the object is then passed through a second lens to produce the inverse of the Fourier transform at the image plane of the second lens. That image is the spatially filtered object. By varying the degree and type of spatial filtering the resultant image can be used to test for contrast sensitivity or character (object) recognition.

BRIEF DESCRIPTION OF DRAWINGS

Other objects, features and advantages of the invention will be apparent from the following detailed description of the invention taken together with the accompanying drawings wherein:

FIG. (FIG.) 1 is a schematic plan view of a vision testing system in accordance with the invention.

FIG. 1A is a graph showing a contrast sensitivity curve of normal vision.

FIG. 1B is a front elevational view of a retractable axle for use in the system of FIG. 1 with changeable variable spatial filters.

FIG. 2 is a schematic of the optical equivalent of the FIG. 1 system, useful in explaining how the invention works.

FIG. 6 is a front elevational view of still another variable spatial frequency filter for character recognition testing but in the form of diverging strips of clear areas on an opaque background.

FIG. 6A is a detailed view of the diverging strips of FIG. 6 taken at the beginning of the diverging strips.

DETAILED DESCRIPTION OF INVENTION

Although the Snellen test can reveal what size letter a subject can recognize, it has no means to measure the level of contrast necessary for recognition at different spatial frequencies nor does it test for recognition with limited spatial frequency information. Contrast is defined as $C = (L_{max} - L_{min})/(L_{max} + L_{min})$, where $L_{max}$ is the peak luminance (measured at the brightest point in a light bar) and $L_{min}$ is the minimum luminance (measured at the darkest point in a dark bar).

Spatial frequency is defined as the number of cycles of a diffraction grating pattern subtended in one degree of visual angle at the eye. A grating of broad lines has low spatial frequency while a grating of closely spaced lines has high spatial frequency.

Subjects with normal vision (as measured by the Snellen test) may or may not have normal contrast sensitivity. The normal contrast sensitivity curve is shown in FIG. 1A, which is based on data from 10 observers. Contrast sensitivity is plotted as a function of spatial frequency on a log/log scale. The high frequency cut-off, or 45 cycles/degree, is marked by a broad arrow and is the extrapolation of the normal contrast sensitivity curve.

There is no correlation between contrast sensitivity and acuity. If one wishes to know if a subject has normal vision in both acuity and contrast sensitivity, both must be measured.

The mathematical theorem of J. B. Fourier can be basically stated: a periodic function can be represented by the sum of sinusoidal functions. Thus a square wave, which varies between $+1$ and $-1$ and has period P can be represented by the Fourier series:

$$f(x) = \frac{4}{\pi}\left(\sin\frac{2\pi x}{P} + \frac{1}{3}\sin 3\frac{2\pi x}{P} + \frac{1}{5}\sin 5\frac{2\pi x}{P} + \ldots\right)$$

Although there are an infinite number of components, the addition of the first four can be shown to yield the basic square wave form. The addition of higher and higher terms leads to a better representation.

Figure 4A:
FIG. 4A is the diffraction pattern at the focal plane of the testing system of FIG. 1 when the square wave grating of FIG. 3 is used as an object to test contrast sensitivity.

The relationship between the function f(x) and its spectrum is the Fourier transformation. If the function is a single slit (or square pulse) the diffraction pattern produced by passing coherent light through the slit is a Fourier analysis of the slit. The Fourier components that contribute most to "build" a square pulse are those of low frequency; in an optical example, the brighter dots closer to the axis (FIG. 4A). The nodal points in the diffraction pattern correspond to those frequencies (spatial frequencies) that do not contribute to the square pulse.

Referring to FIG. 2, the optical equivalent of the present invention shown in FIG. 1, the laser 10 produces coherent light waves which are filtered by the $L_0$ lens 12 (which is part of laser 10) and the pinhole 14 located at the focal point of lens 12 to produce a relatively noise-free beam of light. The pinhole is about twice the diameter of the focused beam, large enough to allow the primary beam to pass through, but small enough to block stray light. Laser 10 is preferably a helium neon laser (wavelength = 632.8 nanometers).

The primary beam of light then passes through $L_c$ lens 16 (f = 0.40 meter) which produces a parallel beam having a diameter of about 25 millimeters. The parallel beam then passes through a transparency 18 of an object. Then the beam passes through $L_1$ lens 20 (1 meter from transparency 18). The lens 20 (focal length f of 1 meter) yields the Fourier transform F(u) of the object on the transparency 18 at its focal plane, or Fourier transform plane F.T. The $L_2$ lens 24 (f = 1 meter, and 1 meter from the F.T. plane) then takes the Fourier transform of the object and, with the inverse transform, displays it in the plane of magnifier lens 26, which is the image plane of lens 24 (located 1 meter from lens 24). An observer's eye at the magnifier lens 26 will then see the image of the object of transparency 18.

It should be noted that the system so far described in detail is disclosed in the publication Physical Optics Using a Helium-Neon Laser by Arthur Eisenkraft, Metrologic Instruments, Inc. 1980, page 44, but with a screen in place of magnifier lens 26 to demonstrate how a continuous tone image can be produced from a halftone dot pattern by proper filtering.

What is believed to be novel is the generation of a sine wave grating of variable contrast from a square wave grating to test for contrast sensitivity.

What is also believed to be novel is the generation of Snellen letters and portraits which have been filtered with variable band pass spatial filters to test for optimum recognition of those objects.

Figure 3:
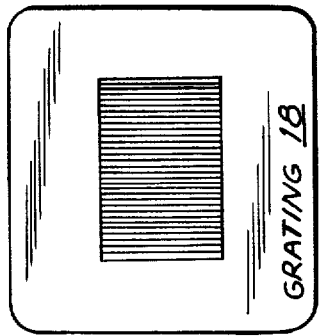
FIG. 3 is a front elevational view of a transparency of a typical square wave grating used as an object in the vision testing system of FIG. 1 to measure contrast sensitivity.

In accordance with the preferred embodiment of the invention, the vision testing system of FIGS. 1, 2 is used to test for contrast sensitivity by using a sequence of variable spatial filters 22A-22P (16 filters) at the Fourier transform plane F.T. and a sequence of corresponding gratings 18A-18P (16 gratings) for object 18. The gratings 18A-18P vary in spatial frequency from 1 cycle/degree to 50 cycles/degree. FIG. 3 shows grating 18 of 4.4 cycles/degree. FIG. 4 shows a generalized variable spatial filter 22.

Variable spatial filter 22 comprises a peripheral clear track 21 and a peripheral variable track 23 of increasing opaqueness, both on an opaque background 25. As is heretofore explained in greater detail, variable spatial filter 22 is rotatably mounted at the Fourier transform plane F.T. Its periphery has contrast sensitivity marks 28 which are suitably correlated with a corresponding part of variable track 23 in the light beam path to provide a measure of contrast sensitivity when the person being tested first recognizes the bars of the grating 18 as the variable spatial filter 22 is rotated, starting from the most opaque portion of variable track 23. Then the vision test is repeated with grating 18 of the next higher spatial frequency and the corresponding variable spatial filter 22, and so on until each of the gratings 18A-18P is used with its corresponding variable spatial filter 22A-22P in testing the vision of the person for one eye. Then the entire test is repeated for the other eye.

Figure 4B:
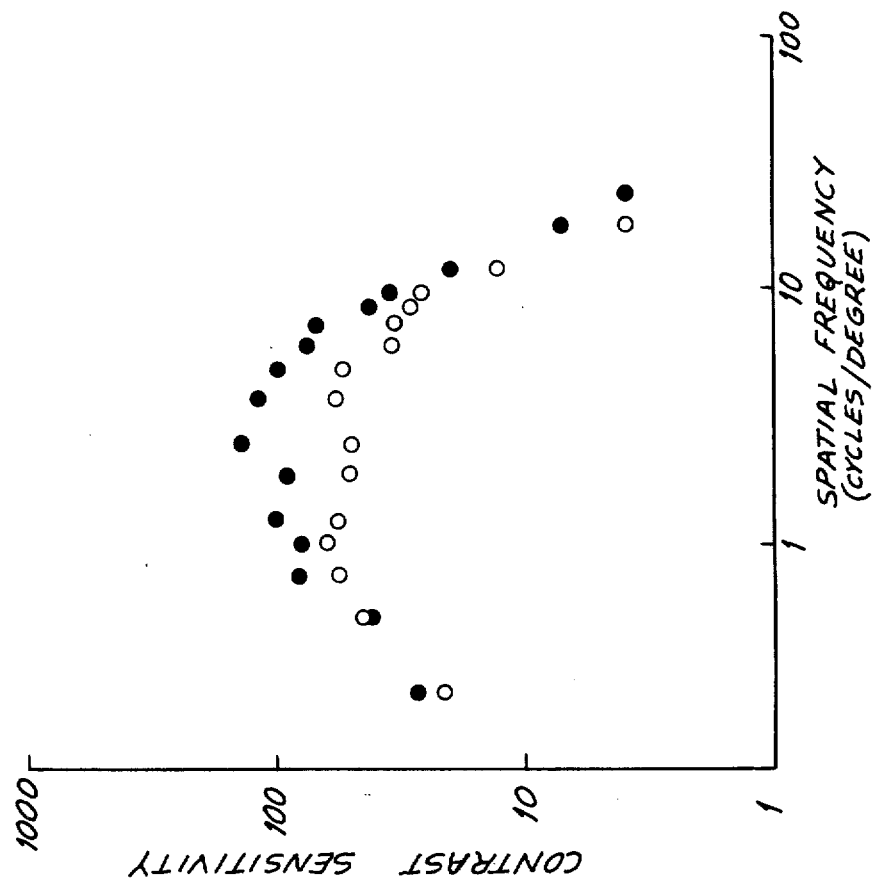
FIG. 4B is a graph showing contrast sensitivity of the right and left eyes of a patient having multiple sclerosis plotted from data obtained with the vision testing system of FIG. 1.
Figure 4:
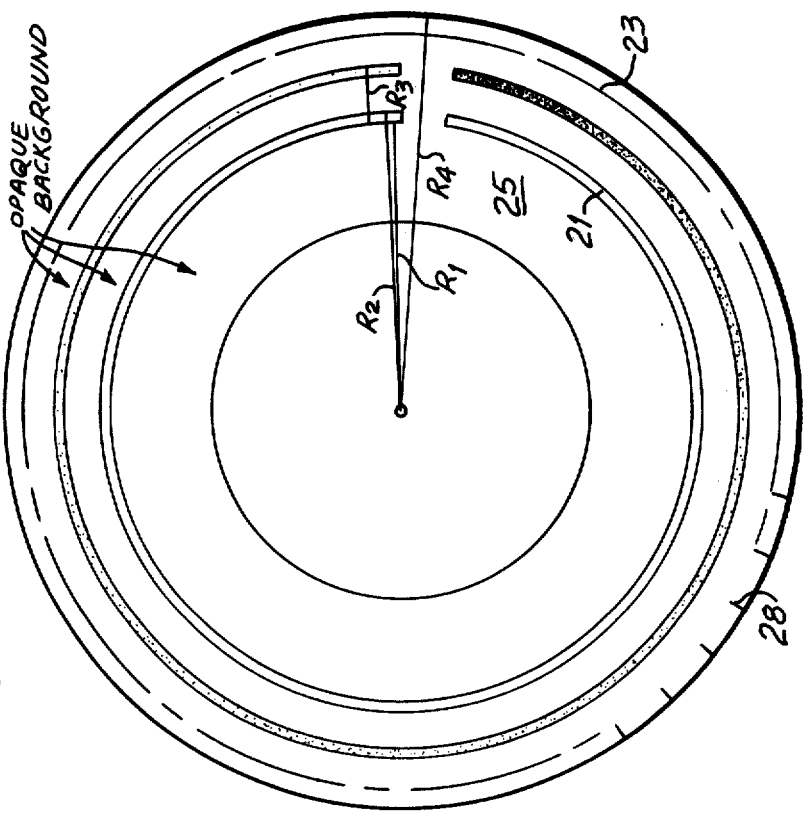
FIG. 4 is a front elevational view of a variable spatial frequency filter in the form of a rotatable disc having one clear and one varying density band on an opaque background, used for testing contrast sensitivity.

The data is then plotted on a graph like that of FIG. 4B. The 16 black dots show the contrast sensitivity for the right eye, and the circles show the contrast sensitivity for the left eye, of a person with multiple sclerosis who has normal acuity. The person's right eye is substantially normal but the contrast sensitivity for the left eye shows a mid-frequency loss.

The diffraction pattern of a grating 18 at the Fourier transform plane F.T. is shown in FIG. 4A. Each diffraction dot to the right or left of the central dot represents a different harmonic. Since the gratings 18 have vertical bars the normal reversal produced by the optical system results in a horizontal diffraction pattern. The narrower the spacing between the vertical grating lines the greater the horizontal spacing between the diffraction dots. The diffraction dot to the right (or the left) of the central dot (or fundamental frequency) represents a substantially pure sine wave of the diffraction pattern. By passing the central dot through the clear track 21 and the first dot through the variable track 23 (FIG. 4) and rotating the variable spatial filter 22 the contrast of the image of the grating at the magnifier lens 26 is smoothly varied until the vertical lines of the grating are recognized. That position is a measure of the contrast sensitivity of the person whose vision is being tested. Plotting those points on a graph like that of FIG. 4B results in the contrast sensitivity curves for each of the person's eyes.

More particularly, variable spatial filter 22 (FIG. 4) changes the square wave grating image diffraction pattern from the square wave to a sine wave grating at the F.T. plane by letting through the zeroth order maximum and first order maximum of the diffraction pattern.

The radial distances of filter 22A for use with corresponding grating 18A are preferably as follows: $R_1 = 64.75$ mm; $R_2 = 65.25$ mm; $R_3 = 0.63$ mm; and $R_4 = 90$ mm. The width of each of the tracks 21 and 23 is 0.5 mm. $R_3$ is dependent on the spatial frequency of the square grating of FIG. 3, where $R_3 = (6328 \times 10^{-7}$ mm$)/d$ and d is the distance between grating lines in meters. For example:

| Grating spatial frequency (cycles/degree) | d | R |
|---|---|---|
| 1.5 | 3.0 mm | .2 mm |
| 15.0 | .3 mm | 2.0 mm |
| 44.0 | .1 mm | 6.0 mm |

The vision testing system of FIGS. 1, 2 can also be used for testing for Snellen character, portrait or other object recognition by using optical band pass filters for the variable spatial filter 22 and a transparency for the object 18.

If a clear aperture on an opaque background is placed in the F.T. plane only low spatial frequencies will get through to contribute to the image at magnifier lens 26. That is equivalent to a low pass filter in electronics. On the other hand an opaque disc on a clear background will allow only high frequencies to contribute to the image. That is equivalent to a high pass filter in electronics. A combination of those in the form of clear annulus on an opaque background would let through only certain spatial frequenices. This is equivalent to a band pass filter.

It is believed novel to use such a system with a variable band pass filter to measure optimum character recognition and testing for threshold recognition.

Figure 5A:
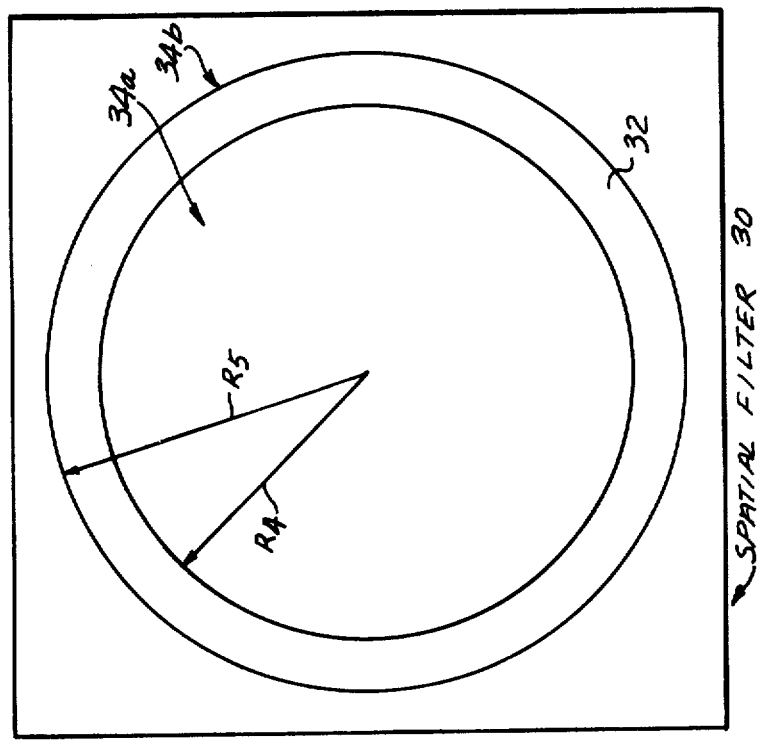
FIG. 5A is a front elevational view of one of the FIG. 5 band pass filter transparencies.
Figure 5:
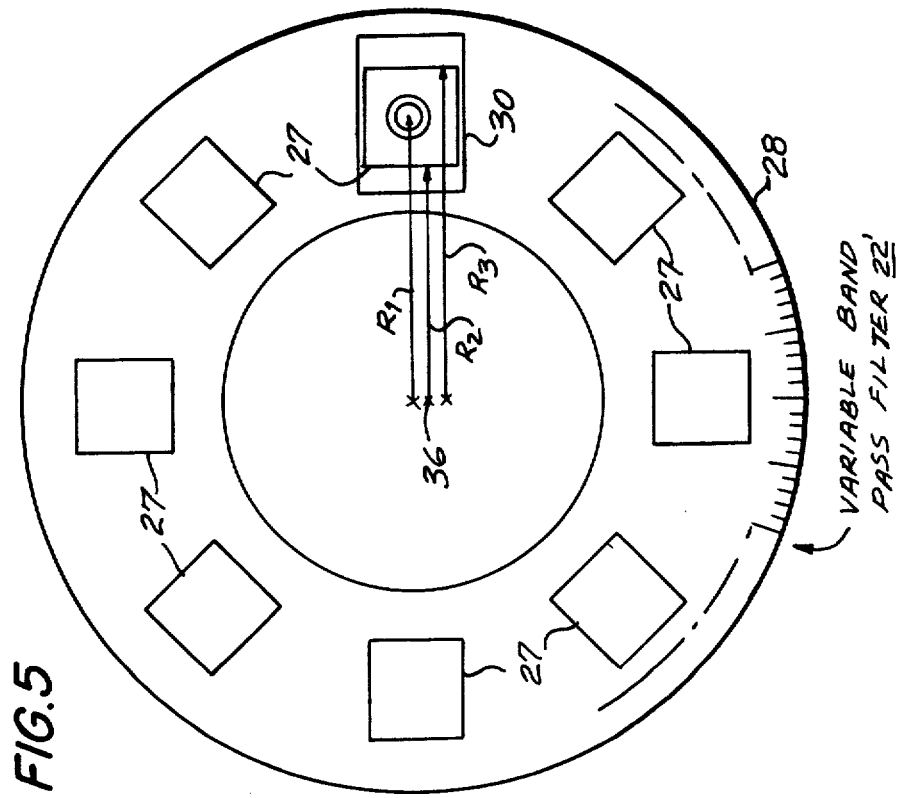
FIG. 5 is a front elevational view of a variable spatial frequency filter employing a sequence of transparencies comprising varying-width clear bands on an opaque background as different band pass filters, for testing for character recognition.

One example of such a variable spatial filter is variable band pass filter 22' shown in FIG. 5. A sequence of transparencies 27 is mounted on a rotatable disc 28, with each transparency consisting of an optical filter like that shown in FIG. 5A as spatial filter 30. Spatial filter 30 consists of a clear annulus 32 on an opaque background 34a,34b. FIG. 5 shows the radial distances $R_1$, $R_2$ and $R_3$ from the axis 36 of the rotatable disc 28 to the spatial filter 30. These radial distances are preferably as follows: $R_1 = 65$ mm, $R_2 50$ mm and $R_3 = 80$ mm. For a variable band pass filter 22' with eight spatial filters 30 (though the larger the number the better measurements), the radial distances $R_4$ and $R_5$ (FIG. 5A) are preferably as follows for a one octave bandpass filter and a two octave filter:

| One Octave Band Pass Filter | | Two Octave Band Pass Filter | |
|---|---|---|---|
| $R_4$ (mm) | $R_5$ (mm) | $R_4$ (mm) | $R_5$ (mm) |
| .2 | .4 | .2 | .8 |
| .4 | .8 | .4 | 1.6 |
| .6 | 1.2 | .6 | 2.4 |
| .8 | 1.6 | .8 | 3.2 |
| 1.0 | 2.0 | 1.0 | 4.0 |
| 1.2 | 2.4 | 1.2 | 4.8 |
| 1.4 | 2.8 | 1.4 | 5.6 |
| 1.6 | 3.2 | 1.6 | 6.4 |

Referring again to FIG. 1, a vision testing system in accordance with the invention is shown. Basically, the optical system of FIG. 2 is packaged in a relatively compact and portable cabinet 40, which encloses the system. Also, variable spatial filter 22 is axially mounted on a support 42 comprising the brackets 42A and 42B and the interconnecting retractable axle 43 (FIG. 1B).

Retractable axle 43 comprises a cylinder 43A on which variable spatial filter 22 turns, post 43B attached to bracket 42B and slidingly engaging the inside of cylinder 43A, and spring 43C to urge cylinder 43 against bracket 42A via annular disc 43D.

Cylinder 43A is retracted from the opening in variable filter 22 to change to another variable filter 22 for contrast sensitivity testing. Detents (not shown) may be used to permit the disc 28 (FIG. 5) of variable bandpass filter 22' to be manually rotated so that spatial filters 30 snap into position at the Fourier transform plane F.T. when the invention is used for object recognition testing. The spatial filters 30 intercept the coherent light beam which passes through the pinhole 14, is collimated into a parallel beam by $L_c$ lens 26, then passes through the transparency 18 of an object (a Snellen character, a portrait or other object) and via front-surfaced mirrors M, is transmitted to the $L_1$ lens 20 which yields the Fourier transform of the diffraction pattern of the object, via additional mirrors M, at the F.T. plane. The light waves are thus spatially filtered by one of the spatial filters 30 (FIG. 5A) on the variable bandpass filter 22'. The spatially filtered lightwaves of the Fourier transform of the diffraction pattern of the object are then transmitted, via additional mirrors M, to $L_2$ lens 24, which takes the inverse of the Fourier transform to produce an image of the object in the plane of (10×) magnifier lens 26. The elements of the optical system within cabinet 40 are spaced optically exactly as shown and described in connection with the FIG. 2 system, with the mirrors M permitting the system including laser 10 to be incorporated into cabinet 40.

The method of testing a person for object recognition is as follows: The person places the eye being tested adjacent the magnifier lens 26 with the variable bandpass filter initially set to provide low pass spatial filtering. Then the person (or the person administering the test) rotates disc 30 from the position with the low pass filtering, through the intermediate filter levels of the spatial filters 30, to the high pass filtering level. The positions of maximum and minimum recognition of the object on transparency 18 are recorded. (The positions between spatial filters 30 are opaque so that a sequence of different images are presented to the person being tested.) The axial positions of maximum and minimum recognizability are correlated with the associated band pass filter to provide a measure of the spatial frequency sensitivity of the person being tested.

Other variable band pass filters 22' may comprise different sets of filters 30. These may be one octave band width filters, two octave band width filters, three octave band width filters, etc., or combinations which change from one octave band width to two octave band width to three octave band width, etc.

An alternative embodiment of variable band pass filter 22' is shown in FIGS. 6 and 6A as variable band pass filter 22" having increasingly diverging clear strips 50A and 50B on an opaque background 52. Radius $R_1$ to the radial midpoint of the strips 50 is preferably 65 mm. $R_2=R_4$ and vary from 0.2 mm to 6 mm. $R_3=R_5$ and vary from 0.4 mm to 12 mm.

Variable band pass filter 22" is positioned in the F.T. plane of the vision testing system shown in FIG. 1 and is supported on axle 42C in the same way as variable band pass filter 22'. Variable band pass filter 22" continuously varies the band pass and thus the spatial frequency filtering. Calibrations 54 at its periphery provide a measure of the filtering and thus an indication, at minimum and maximum recognition positions of the image of the object, of character recognition ability of the person being measured. Since filter 22" is capable of continuous variation there is no detent mechanism corresponding to that needed for variable band pass filter 22' of FIG. 1.

When the vision testing system of FIGS. 1, 2 is used to test contrast sensitivity the variable spatial filter 22 (FIG. 4) must be changed to correspond with the grating 18 for each spatial frequency test. The peripheral channels 21 and 23 of each variable spatial filter 22 are in the path of the central and first order dots of the grating diffraction pattern (FIG. 4A) at the F.T. plane (FIG. 1).

The variable filters 22, 22' and 22" may be readily created by photographing black and white drawings on Kodalith or High Contrast copy film.

For group testing, or for persons whose vision prevents them from focusing on a small slide, the magnifier lens 26 may be replaced by a television camera (without a lens since the light pattern is already focused) fitted to the image plane and a much larger image can be displayed on a monitor.

In addition to vision testing the invention has other uses.

Reading problems related to distracting spatial frequency bands could be investigated by using the optical spatial filter to eliminate distracting spatial frequency bands from reading materials.

Displays and targets could also be rapidly altered by an optical spatial filter which would lead to improvements in signal detection, especially for military applications. Increasing the contrast of relevant specific spatial frequencies can improve identification of displayed images.

The vision test can also yield information about how to optimally mask displays as in camouflage.

Those skilled in the art may be able to make other modifications and uses of the illustrated embodiments of the invention and devise other specific structures for incorporating its principles. It is to be understood that it is intended to cover all such changes and modifications which do not constitute a departure from the true spirit and scope of the invention.

What is claimed is:
1. A method of testing a person's vision comprising the steps of:
 (A) passing a collimated beam of coherent light waves through a transparency of an object to produce its diffraction pattern;
 (B) passing those light waves forming the diffraction pattern through a first lens to produce the Fourier transform of the object at the Fourier transform plane of the first lens;
 (C) spatially filtering at the Fourier transform plane of the first lens the light waves forming the Fourier transform of the object;
 (D) passing the spatially filtered lightwaves of the Fourier transform of the object through a second lens to produce the inverse of the Fourier transform at the image plane of the second lens as an image of the object; and

(E) varying the spatial filtering to vary the recognizability of the image of the object by the person being tested;

(F) whereby the relationship between the degree of spatial filtering and the recognizability of the image of the object is a measure of the vision of the person being tested.

2. The method of testing a person's vision according to claim 1 wherein said object is a grating and recognition of the image of the grating is a measure of that person's contrast sensitivity.

3. The method of testing a person's vision according to claim 1 wherein said object is a character and the amount of recognizability of the image of the character is a measure of that person's vision.

4. The method of testing a person's vision according to claim 2 wherein spatial filtering at the Fourier transform plane of the first lens is performed by an opaque rotatable disc having one clear peripheral track and one peripheral track of increasing opaqueness.

5. The method of testing a person's vision according to claim 4 wherein the central dot of the diffraction pattern of the grating at the Fourier transform plane of the first lens passes through the clear peripheral track and an adjacent dot passes through the peripheral track of increasing opaqueness to vary the contrast of the image of the grating at the image plane of the second lens by rotating the opaque rotatable disc.

6. The method of testing a person's vision according to claims 3, 4 or 5 by testing for grating recognizability with a sequence of gratings of different spatial frequency.

7. The method of testing a person's vision according to claim 3 whereby the spatial filtering of the light waves forming the Fourier transform of the object is varied until the image of the object is first recognizable.

8. The method of testing a person's vision according to claim 3 whereby the spatial filtering of the light waves forming the Fourier transform of the object is varied until the image of the object is best recognizable.

9. The method of testing of person's vision according to claim 3 whereby the spatial filtering of the light waves forming the Fourier transform of the object is varied until the image of the object is best recognizable and also until the image of the object is no longer recognizable.

10. The method of testing a person's vision according to claim 3 wherein the degree of spatial filtering is varied by a rotatable disk having a sequence of optical bandpass filters.

11. The method of testing a person's vision according to claim 10 wherein said sequence of optical filters comprises a plurality of optical bandpass filters for incrementally changing the amount of spatial filtering.

12. The method of testing a person's vision according to claim 3 wherein the degree of spatial filtering is varied by a rotatable disk comprising a continuously variable band pass filter.

13. The method of testing a person's vision according to claim 12 wherein said continuously variable band pass filter comprises a disc having a plurality of diverging clear bands on an opaque background.

14. A system for testing a person for vision contrast sensitivity comprising:

(A) a source of coherent light waves;
(B) collimating means for collimating said coherent light waves into a collimated beam of light;
(C) a transparency of a grating for changing said collimated beam of light into a diffraction pattern of said grating;
(D) a first lens for yielding the Fourier transform of said grating at the Fourier transform plane of said first lens;
(E) a variable spatial filter positioned at said Fourier transform plane for spatially filtering the light waves at said plane;
(F) a second lens responsive to said spatially filtered light waves for yielding the inverse of said Fourier transform of said grating; and
(G) an imaging means responsive to said inverse Fourier transform to display said spatially filtered light waves as an image of said grating;
(H) whereby the degree of spatial filtering when the image of said grating is recognized is a measure of the contrast sensitivity of the person being tested.

15. A system for testing a person for vision contrast sensitivity according to claim 14 wherein said variable spatial filter comprises a band of increasing density on an opaque background.

16. A system for testing a person for vision contrast sensitivity according to claim 15 wherein said variable spatial filter further comprises a clear band.

17. A system for testing a person for vision contrast sensitivity according to claim 14 wherein said variable spatial filter comprises a rotatable opaque disc having one clear peripheral track and one peripheral track of increasing opaqueness.

18. A system for testing a person for vision contrast sensitivity according to claim 14 wherein said imaging means is a magnifier lens.

19. A system for testing a person for vision contrast sensitivity according to claim 14 wherein said imaging means comprises a television camera and monitor.

20. A system for testing a person for object recognition comprising:

(A) a source of coherent light waves;
(B) collimating means for collimating said coherent light waves into a collimated beam of light;
(C) a transparency of an object for changing said collimated beam of light into a diffraction pattern of said object;
(D) a first lens for yielding the Fourier transform of said object at the Fourier transform plane of said first lens;
(E) a variable band pass filter positioned at said Fourier transform plane for spatially filtering the light waves at said plane;
(F) a second lens responsive to said spatially filtered light waves for yielding the inverse of said Fourier transform of said object; and
(G) an imaging means responsive to said inverse Fourier transform to display said spatially filtered light waves as an image of said object;
(H) whereby the degree of spatial filtering when the image of said object is recognized by the person being tested is a measure of the vision of the person being tested.

21. A system for testing a person for object recognition according to claim 20 wherein said variable band pass filter comprises a sequence of optical filters.

22. A system for testing a person for object recognition according to claim 20 wherein said variable band pass filter comprises a sequence of optical filters positioned along radii of a rotatable disc.

23. A system for testing a person for object recognition according to claim 20 wherein said variable band pass filter comprises a plurality of diverging clear bands on an opaque background.

24. A system for testing a person for object recognition according to claim 20 wherein said object is a portrait.

25. A system for testing a person for object recognition according to claim 20 wherein said object is a Snellen letter.

* * * * *